United States Patent
Wirth et al.

(10) Patent No.: US 8,450,102 B2
(45) Date of Patent: May 28, 2013

(54) DEVICE AND METHOD FOR STABILISING THE FLOW THROUGH A CHAMBER

(75) Inventors: Andreas Wirth, Lengerich (DE); Michael Kazinski, Cologne (DE)

(73) Assignee: Lonza Cologne GmbH, Cologne (DE)

(*) Notice: Subject to any disclaimer, the term of this patent is extended or adjusted under 35 U.S.C. 154(b) by 1497 days.

(21) Appl. No.: 12/035,960

(22) Filed: Feb. 22, 2008

(65) Prior Publication Data
US 2008/0213854 A1 Sep. 4, 2008

Related U.S. Application Data

(60) Provisional application No. 60/891,266, filed on Feb. 23, 2007.

(30) Foreign Application Priority Data

Feb. 23, 2007 (EP) .................................... 07003739

(51) Int. Cl.
*C12M 1/42* (2006.01)
*C12N 13/00* (2006.01)

(52) U.S. Cl.
USPC .................. 435/285.2; 435/173.6; 435/293.1

(58) Field of Classification Search
USPC ........................................... 435/173.6, 285.2
See application file for complete search history.

(56) References Cited

U.S. PATENT DOCUMENTS

| | | | |
|---|---|---|---|
| 4,154,668 A * | 5/1979 | Zimmermann et al. | ... 435/285.2 |
| 5,098,843 A | 3/1992 | Calvin | |
| 5,612,207 A * | 3/1997 | Nicolau et al. | ............ 435/173.6 |
| 5,965,410 A | 10/1999 | Chow et al. | |
| 6,150,148 A | 11/2000 | Nanda et al. | |

FOREIGN PATENT DOCUMENTS

JP 63059892 A * 3/1988

* cited by examiner

*Primary Examiner* — William H Beisner
(74) *Attorney, Agent, or Firm* — Joyce von Natzmer; Agris & von Natzmer LLP

(57) ABSTRACT

A device 1 with at least one electrode 8 for generating an electrical field in a chamber 7 is disclosed. The device 1 comprises at least one input channel 6 for introducing a fluid into the chamber 7, and at least one output channel 11 for discharging the fluid from the chamber 7. Also disclosed is a method for stabilizing the flow of a fluid through a chamber 7 in which an electrical field is generated and which has at least one input channel 6 for introducing the fluid into the chamber and at least one output channel 11 for discharging the fluid from the chamber 8. To avoid undesirable backflow of the fluid due to gas formation, the average inside diameter of the input channel 6 of device 1 is smaller than the average inside diameter of the output channel 11.

11 Claims, 4 Drawing Sheets a)

b)

c)

d)

e)

a)
b)
c)
d)
e)

DEVICE AND METHOD FOR STABILISING THE FLOW THROUGH A CHAMBER

CROSS-REFERENCE TO RELATED APPLICATIONS

This application claims the benefit of U.S. provisional application 60/891,266, filed Feb. 23, 2007, which is incorporated herein by reference in its entirety. This application claims priority from European application EP 07 003 739.5, also filed on Feb. 23, 2007.

FIELD OF THE INVENTION

The invention relates to a device with at least one electrode for generating an electrical field in a chamber, at least comprising at least one input channel for introducing a fluid into the chamber, and at least one output channel for discharging the fluid from the chamber. The invention also relates to a method for stabilising the flow of a fluid through a chamber in which an electrical field is generated and which has at least one input channel for introducing the fluid into the chamber and at least one output channel for discharging the fluid from the chamber.

BACKGROUND OF THE INVENTION

The introduction of biologically active molecules, for example DNA, RNA or proteins, into living cells may, e.g., serve to examine the biological functions of these molecules and is, moreover, an essential precondition for the success of the therapeutic use of these molecules, e.g., in gene therapy. A preferred method for introducing external molecules into the cells is called electroporation, which unlike chemical methods limits undesirable changes in the structure and function of the target cell. In electroporation the external molecules are introduced into the cells from an aqueous solution, preferably a buffer solution specifically adapted to the cells, or a cell culture medium, via a short current flow, i.e., e.g., the pulse of a discharging capacitor which renders the cell membrane permeable to the external molecules. The temporary "pores" that are formed in the cell membrane allow the biologically active molecules to first reach the cytoplasm in which they may already perform their function or exert any therapeutic action to be examined, and then, under certain conditions, to also reach the cell nucleus as it is required, e.g., in gene therapy applications. Due to the short application of a strong electrical field, i.e. a short pulse with a high current density, cells, cell derivatives, sub-cellular particles and/or vesicles may also be fused. In this so-called electrofusion the cells are, e.g., initially brought into close membrane contact by an inhomogeneous electrical alternating field. The subsequent application of an electrical field pulse leads to interaction between membrane parts, which ultimately results in fusion. Devices comparable to those used for electroporation may be used for electrofusion.

Smaller volumes are generally treated in a batch process in relatively simple vessels. The solution or cell suspension, respectively, is frequently located in a cuvette, i.e. a narrow vessel open at the top, which in the vicinity of the bottom has two opposing, parallel electrodes in the lateral walls which serve to apply the electrical voltage. However, such vessels are unsuitable for treating larger volumes as the reaction space available for the electrical treatment is limited by the limited maximal distance between the electrodes. Thus, flow-through processes in which the cell or vesicle suspension is continuously or discontinuously fed through the reaction space between the electrodes are preferred for the electroporation or electrofusion of larger volumes.

U.S. Pat. No. 6,150,148, for example, discloses a cuvette modified for flow-through processes. The port of the cuvette is sealed by a cap through which a feed line is guided. At the bottom in a region between the electrodes the cuvette has an additional port to which a discharge is connected. Because of this arrangement the suspension to be treated can be fed through the feed line into the reaction space and exit it through the discharge. Due to repeated, continuous or discontinuous exchange of the suspension in the reaction room and the respective repeated pulsing, larger volumes can be treated with this cuvette.

U.S. Pat. No. 6,150,148 also discloses flow-through chambers which are of tubular or slotted design and at their ends each have a connection for an input and an output channel. The chambers themselves represent an oblong reaction space which is enclosed by two cylindrical, concentrically arranged or flat electrodes having plane-parallel configuration. These devices also allow larger volumes to be treated by repeated pulsing as they are fed through the chamber.

All references mentioned herein are incorporated herein by reference in their entirety.

During electroporation or electrofusion in flow-through processes the formation of gas bubbles by electrolysis poses, next to heating of the suspension, a significant problem. The very high currents that are often required for these processes leads to large numbers of small gas bubbles that are formed by electrochemical processes in the electrolyte solution in which the cells or vesicles to be treated are suspended. These bubbles disturb the flow of the suspension through the chamber and may result in a backflow of the suspension already treated into the chamber. This, on the one hand, leads to results that are no longer reproducible and on the other hand, if living cells are treated, to an increased mortality rate.

Thus, there is a need for a device and a method for flow-through electroporation or electrofusion in which a directed flow of the fluid to be treated through the chamber or reaction zone is guaranteed and a backflow of the fluid already treated into the chamber or the reaction zone, respectively can be avoided.

SUMMARY OF THE INVENTION

The present invention addresses this and other needs which will become apparent from the following disclosure and claims by providing in the devices already mentioned that the average inside diameter of the input channel is smaller than the average inside diameter of the output channel. The above and other needs are also addressed with regard to the method mentioned above, in that the input channel is diminished to reduce its inside diameter. By providing an upstream inside diameter that is smaller on the access side, the pressure in front of the chamber (upstream) is increased compared to the pressure behind the chamber (downstream), so that the flow of the fluid is generally stabilised in terms of its direction. Due to this pressure gradient gas bubbles or fluid are advantageously prevented from flowing from the output channel back into the chamber. According to the invention the average inside diameter of the input channel, compared to the average inside diameter of the output channel, is chosen so that the pressure upstream of the chamber is always higher than downstream of the chamber. In the simplest case the inside diameter of the input channel is smaller throughout its length than the inside diameter of the output channel throughout its length or at its narrowest point. However, the inside diameter of the input channel may, e.g., also be or become reduced at a particular point or within a limited section relative to the inside diameter of the output channel if both channels otherwise have approximately the same inside diameter. The diminution of the inside diameter of the input channel represents a simple, low cost measure which renders the use of complicated, electronically controlled valve systems superfluous.

In a preferred embodiment of the device according to the invention the inside diameter of the input channel is smaller, at least one point, than the smallest inside diameter of the output channel. The inside diameter of the input channel may therefore be smaller than the narrowest point of the output channel throughout the length of the same or only within at least one section or at least one point. In this embodiment it can be ensured, by relatively simple means, that the pressure is, in the direction of the flow, in each case higher in front of the chamber than behind the chamber.

For example, the input channel may have at least one diminution to reduce its inside diameter. In this case the diminution may be formed by reducing the outside diameter of the input channel while maintaining at least approximately the wall thickness. Additionally or alternatively, the diminution may be formed via elevations, bulges or the like arranged inside the input channel. The insertion of tubes or small pipes with a lower diameter into the input channel is also possible. Furthermore, in a particularly preferred embodiment of the invention, a variable sealing device, for example a slide, flap, valve or diaphragm may be installed in or at the input channel. Via this variable sealing device the inside diameter of the input channel can be adjusted manually or automatically.

In a further preferred embodiment of the device according to the invention provision is made for the output channel to be designed in the shape of an arc or curve in order to prevent the formation of edges and/or dead spaces on or in which cell constituents or cellular debris could accumulate. The treatment of, in particular, living cells with electrical current or the feeding of the same through an electrical field always results in the killing or destruction of individual cells. Thus, not only intact cells but also cell debris, and consequently also intracellular constituents, are to be found in the fluid in the output channel downstream of the chamber. Those can deposit at suitable points and can thus even result in blockage of the output channel. To avoid this the output channel should have no right-angled changes of direction, even if a change of direction is necessary for design reasons.

To ensure that the gas bubbles formed in the fluid resulting from the electrical treatment are able to escape without any problem, the port of the output channel should preferably be arranged above the chamber. Consequently the output channel should also preferably be arranged above the input channel and not at the same height.

Furthermore, the device according to the invention may have a housing, with the openings of the output and input channels being on the surface or outside of the housing for safety reasons. This design ensures that a person operating the device cannot or does not have to reach into the interior of the housing in which the electrodes and other possibly electrically charged components are located. In such a device, connecting of a reservoir and a collection tank is therefore be accomplished without risk. For practical reasons, the ports of both channels should be located on the same side of the housing, preferably the forward or front side, to facilitate handling of the device of the invention.

In addition to the measures described above, the output channel and/or the input channel may be provided with at least one actively controlled or passive valve, preferably at least one check valve. This allows backflow of the fluid into the chamber to be prevented if for some reason the pressure conditions are reversed.

For safety reasons, the input channel and/or the output channel is, according to the invention, provided with at least one earthing electrode. This can prevent the high currents that, in many applications, flow in the device according to the invention from representing a risk to operating personnel. One or a plurality of earthing electrodes may in this case be arranged at any point upstream, downstream of and/or directly on the chamber.

In a particularly preferred embodiment of the device according to the invention the at least one electrode is provided, on its side facing away from the fluid, with at least one cooling device. Since a multiplicity of voltage pulses must be generated when larger quantities of fluid flow through the chamber, the electrodes, and hence also the fluid, are necessarily heated. In order to keep this heating within limits and prevent an increase in the fluid temperature to a temperature that is harmful to the biological materials to be treated, cooling of at least the electrodes is required. For example, the temperature should not rise above 40° C. when treating living cells with electrical current. The electrode(s) can, for example, be cooled by a conventional CPU cooler, a Peltier element or the like. in a preferred embodiment of the invention, for safety reasons a non-current-conducting, heat-conducting film may be arranged between the electrode and the cooling device for insulation.

The invention also relates to a preferred use of the device according to the invention for the electroporation or electrofusion of cells, cell particles and/or membrane vesicles in a flow-through process. Here, the device according to the invention advantageously allows the treatment of large volumes of the biological material by the continuous or discontinuous feeding of the suspension concerned through the chamber.

In a preferred embodiment of the method according to the invention, the diminution is achieved by reducing the outside diameter of the input channel, while, at least approximately, maintaining its wall thickness and/or by inserting elevations, bulges or the like in the input channel.

Particularly preferred is an embodiment of the method according to the invention in which the reduction of the inside diameter of the input channel is varied. The inside diameter of the input channel can in this case be adjusted by manual or automatic actuation of a slide, a flap, a valve, a diaphragm or similar sealing device so that the pressure conditions in the device according to the invention are perfectly adapted to the prevailing conditions. This allows the flow of the fluid to be controlled by varying the inside diameter of the input channel so that an optimum relation between upstream excess pressure on the one hand and the flow rate on the other under different conditions can be set.

In order to limit heating of the fluid as it flows through the electrical field in the chamber, and prevent the fluid temperature from rising to a temperature that is damaging to the material to be treated, provision is made for at least one electrode, provided for generating the electrical field in the chamber, to be cooled.

In the method according to the invention the fluid can be fed continuously or discontinuously through the chamber. Here, a series of electrical fields is generated in the chamber so that each partial volume of the fluid is exposed to the electrical field. The flow rate must be matched to the distances between the individual voltage pulses, or conversely the distances between the individual voltage pulses must be adapted to the flow rate so that a partial volume of the fluid to be treated is subjected as accurately as possible to the desired number of electrical pulses. In any case a situation should be avoided where too high a proportion of the fluid to be treated is exposed to the voltage pulses more frequently than desired or is not treated at all. The fluid preferably contains cells, cell particles and/or membrane vesicles which are exposed to at least one electrical field when fed through the chamber.

BRIEF DESCRIPTION OF THE DRAWINGS

The invention is described in more detail below, by way of example, with reference to the following figures.

DETAILED DESCRIPTION OF VARIOUS AND PREFERRED EMBODIMENTS OF THE INVENTION

Figure 1:
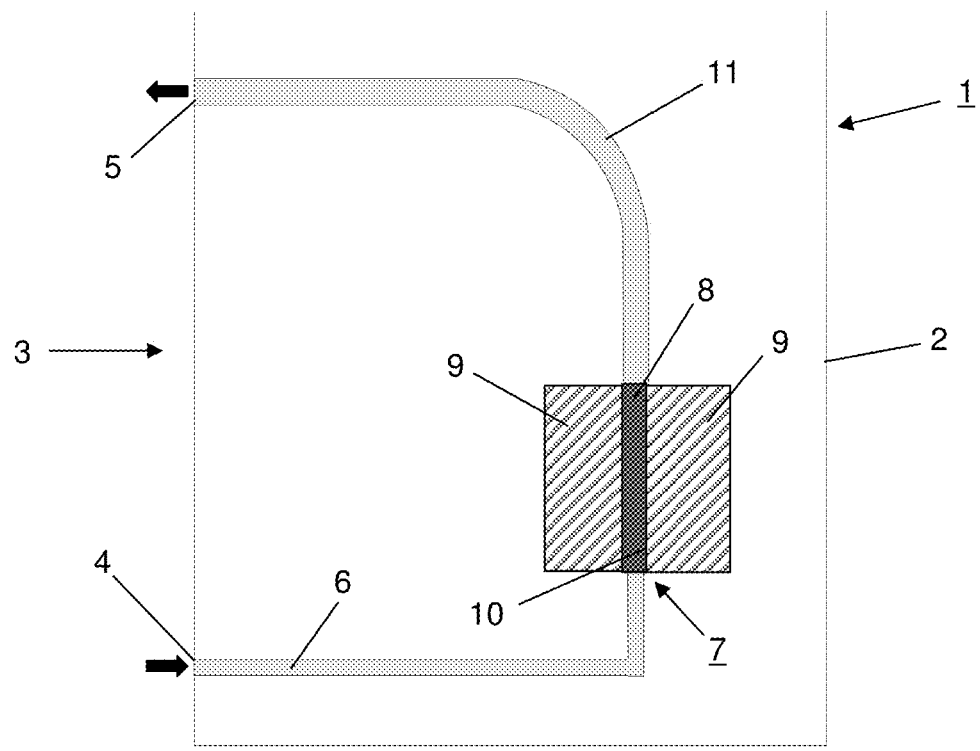
FIG. 1 shows a diagrammatic longitudinal section through an embodiment of the device according to the invention.

FIG. 1 shows a longitudinal section through an exemplary embodiment of the device according to the invention. Device 1 comprises a housing 2 which has 2 ports 4, 5 on its front side 3. Vessels can be connected to ports 4, 5, preferably by tubes or other lines, which each serve to receive a fluid. For example, a storage vessel or reservoir, from which the fluid is introduced into input channel 6 of device 1, preferably by means of a pump or compressed air, can be connected to port 4 (The arrows at ports 4, 5 indicate the direction of flow of the fluid). The fluid is then fed through input channel 6 into a chamber 7, which has two electrodes which are in contact with interior 10 of chamber 7. Of the electrodes, only electrode 8, arranged behind interior 10 of chamber 7, is visible in this representation, whilst the second electrode, which is arranged plane parallel to electrode 8, lies in front of the plane of intersection. The two electrodes are separated from each other by two isolators 9, both of which form, in the extension of input channel 6, a gap which constitutes interior 10 of chamber 7. Interior 10 of chamber 7 is therefore, when viewed from front side 3 of device 1, laterally limited by the electrodes and at the front and rear by isolators 9 located between the electrodes. When an electrical voltage is applied to the electrodes an electrical field, which acts on the material contained in the fluid, is generated in interior 10. The applied voltage is preferably a high voltage pulse which is generated by the discharge of one or a plurality of capacitors. The discharge of the capacitor generates a temporary, strong electrical field between the electrodes in interior 10 of chamber 7.

If the fluid is, e.g., a suspension in which cells, cell particles and/or membrane vesicles are suspended in an electrolyte solution and in which biologically active molecules are dissolved, these biologically active molecules can be introduced into the cells, cell particles and/or membrane vesicles via the electrical field (electroporation). Alternatively the cells, cell particles and/or membrane vesicles can also be fused by the electrical field ((electrofusion). If larger volumes of the fluids or suspension are fed continuously or discontinuously through chamber 7, electrical fields must be generated at short intervals so that each partial volume of the fluid or suspension is exposed to at least one electrical field and can be treated as desired.

The treated material from chamber 7 then reaches the output channel 11 of device 1. Output channel 11 is designed in the shape of an arc and therefore opens into port 5 on front side 3 of device 1. Since in the case of a cell suspension the fluid also contains cell debris after the electrical treatment in chamber 7, a right-angled design of the output channel could result in deposits at the corners and edges that would exist and could in a worst case scenario lead to a blockage of the output channel. Because of the rounded design of output channel 11 of device 1, such problems can be effectively avoided because no cell debris can deposit in the curve regions of output channel 11. For example, a trapping or collection container can be connected to port 5. In this container the fluid or suspension can be collected after treatment in device 1. With storage and collection vessels connected to ports 4, 5, device 1 according to the invention therefore represents a closed system which can also be operated in a sterile manner.

As a result of the electrical field in interior 10 of chamber 7 between the electrodes, gas bubbles may be formed in the fluid due to electrolysis. These bubbles may disturb the flow of the fluid. In particular, if there is a multiplicity of high voltage pulses an excess pressure may develop in chamber 7, which forces the gas bubbles and material already treated back into input channel 6. To avoid this undesirable effect the average inside diameter of input channel 6 is smaller in the device according to the invention than the average inside diameter of output channel 11. In the embodiment shown here both input channel 6 and output channel 11 have an approximately constant inside diameter throughout their length. Since the inside diameter of input channel 6 is much smaller than the inside diameter of output channel 11, a higher pressure builds up when the fluid flows through, upstream of chamber 7 in input channel 6 than downstream of chamber 7 in output channel 11. This pressure gradient advantageously ensures that the flow of the fluid remains constant directed in the direction of the arrows and no fluid already treated is able to flow back into chamber 7 or input channel 6.

As an additional advantageous measure, opening or port 5 of output channel 11 is located above input channel 6 and also above chamber 7 in device 1 according to the invention. This facilitates the escape of the gas bubbles from output channel 11. In addition, a check valve (not shown here) can be arranged in output channel 11, preferably in the vicinity of chamber 7. This valve prevents the fluid from flowing back if the pressure is reversed for a short time, for example when the pump is switched off, or between voltage pulses. Since ports 4, 5 of channels 6, 11 are both arranged on the front side 3 of device 1, the required vessels can easily be connected to device 1. Device 1 is therefore very operator friendly, and also very safe, because the vessels or hoses required cannot be connected directly to chamber 7, but only to housing 2. This eliminates any risk to the operating personnel due to the voltage source or the electrodes.

Figure 2:
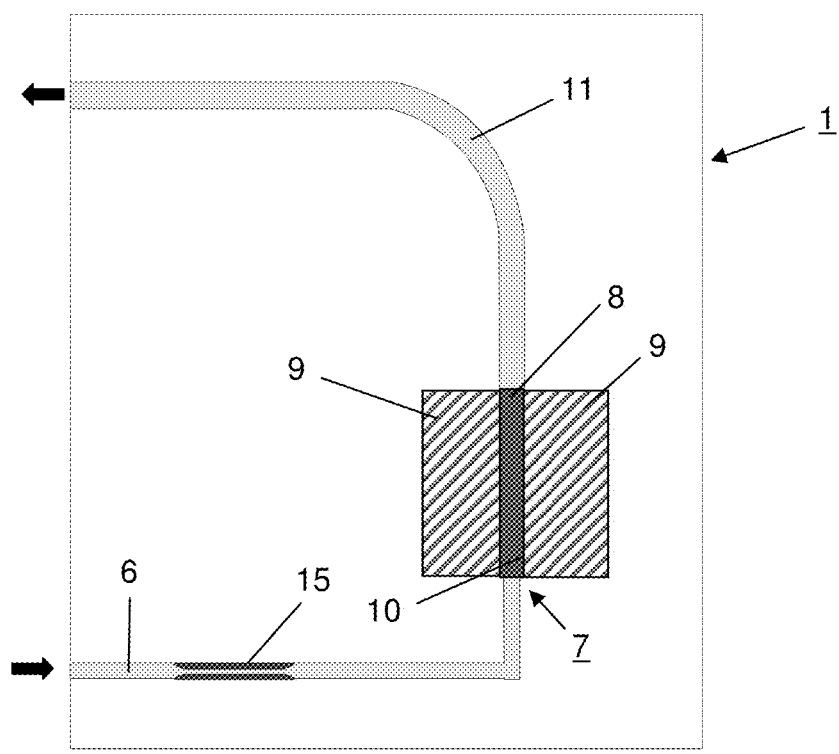
FIG. 2 shows the device according to FIG. 1 with additional diminution of the input channel.

FIG. 2 shows device 1 according to FIG. 1 with diminution 15 additionally inserted in input channel 6. In this embodiment the inside diameter of input channel 6 is therefore again reduced relative to the inside diameter of output channel 11 in the region of diminution 15, so that the pressure gradient is further increased. Because of the additional increase in fluid pressure in input channel 6, fluid can be prevented from flowing back into interior 10 of chamber 7 or input channel 6, respectively, even if there is a very high degree of gas formation in chamber 7. Diminution 15 is an inwardly directed, cylindrical thickening of the wall of input channel 6, with the outside diameter remaining constant. Diminution 15 is therefore a type of bulge or elevation of the inner wall of input channel 6. Alternatively the same effect can also be achieved, for example, by inserting a short piece of tube into input channel 6, in which case the outside diameter of the piece of tube should be equal to or slightly larger than the inside diameter of the input channel (interference fit).

Figure 3:
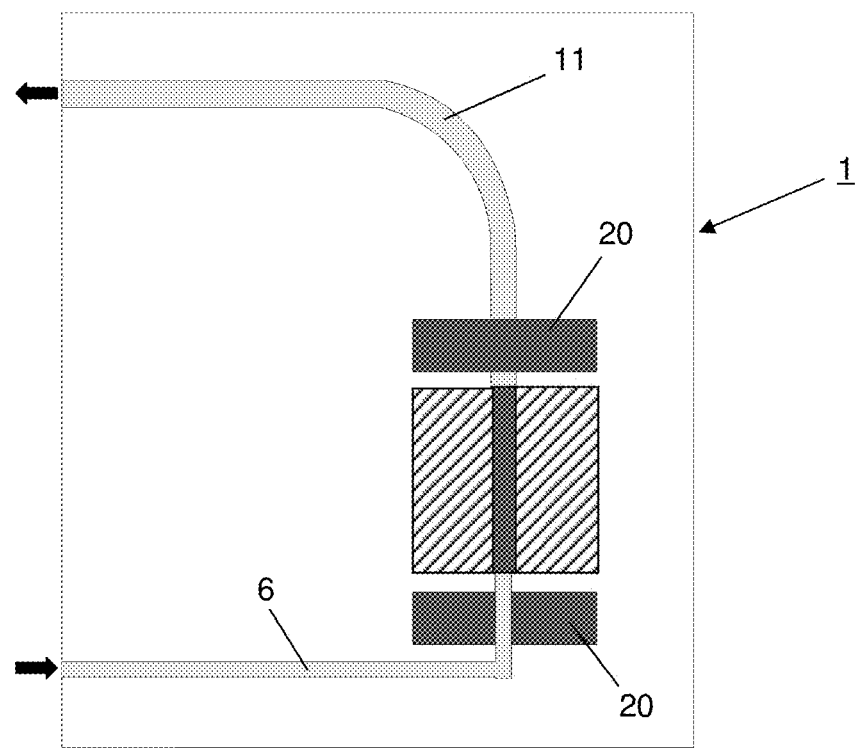
FIG. 3 shows the device according to FIG. 1 with earthing electrodes.
Figure 4:
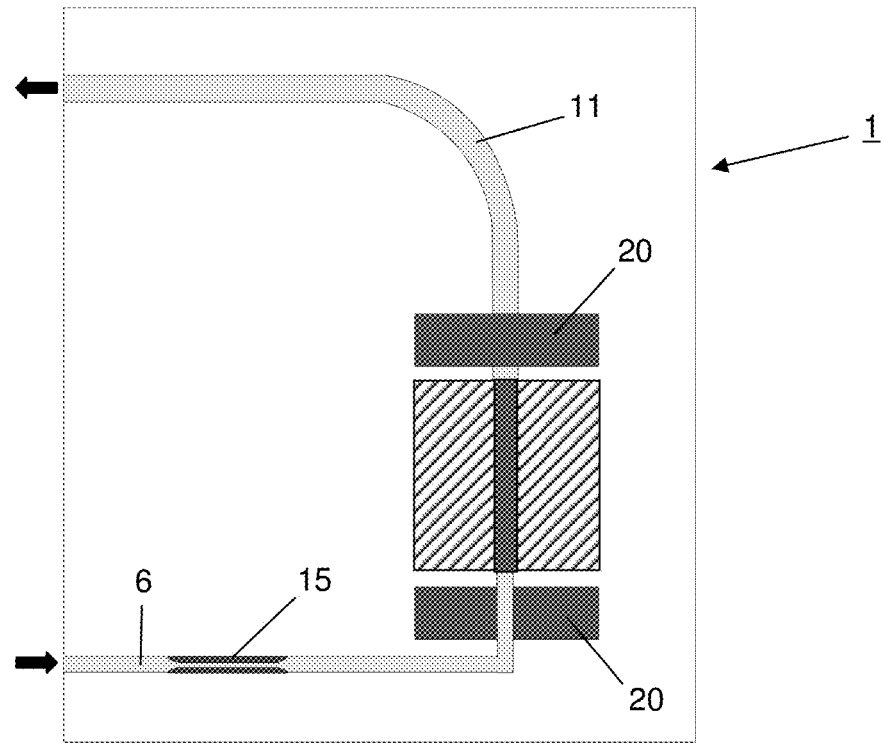
FIG. 4 shows the device according to FIG. 2 with earthing electrodes.

FIGS. 3 and 4 show devices 1 according to FIGS. 1 and 2, each with earthing electrodes 20. The earthing electrodes ensure that device 1 according to the invention is safe. The high currents that in many applications flow in device 1 according to the invention represent a permanent risk to the operating personnel. One or a plurality of earthing electrodes may be arranged at any point downstream, upstream of and/or directly on the chamber in order to reduce the risk of electric shock. Earthing electrodes 20 are installed on both sides of chamber 7 on input and output channels 6, 11, so that currents flowing out of chamber 7 can be directly discharged.

Figure 5:
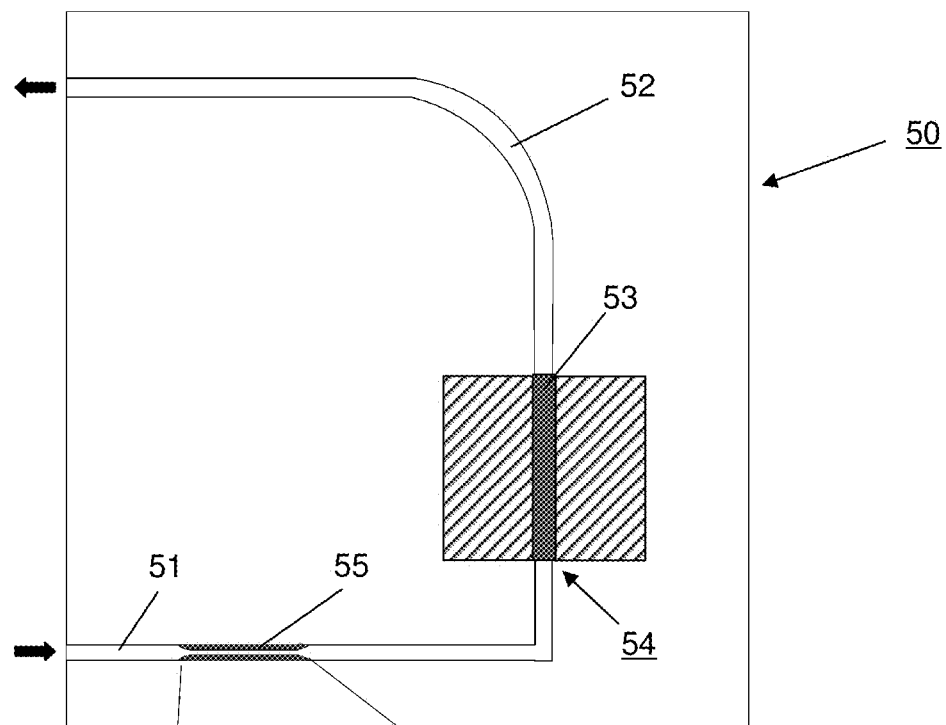
FIG. 5 shows a diagrammatical longitudinal section through further embodiments of the device according to the invention with different diminutions of the input channel.
Figure 5:
Figure 5:
Figure 5:
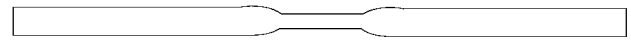

FIG. 5 shows a longitudinal section through a further embodiment of the device according to the invention with different diminutions of the input channel. Unlike device 1 according to FIGS. 1 to 4, device 50 has an input channel 51 and an output channel 52 with approximately the same inside (and outside) diameter. The pressure which is generated by the voltage pulses and the gas bubbles formed thereby in interior 53 of chamber 54 and in output channel 52 is overcompensated for by a diminution 55 in input channel 51, which diminution corresponds essentially to diminution 15 according to FIGS. 2 and 4. Because of the reduction in average inside diameter of input channel 51 compared to the average inside diameter of output channel 52 due to diminution 55, a directed flow of the fluid through chamber 54 can be maintained even with a high gas formation. The reduction in the average inside diameter of input channel 51 can be achieved in different ways, as demonstrated by the different embodiments according to a) to e). Whilst the embodiments according to b) and e) are in principle similar to the embodiment according to c), the diminution in the embodiment according to d) is achieved by reducing the outside diameter of the input channel while maintaining the wall thickness. Such an effect can also be achieved, for example, by fitting a clamp or the like on a flexible section of the input channel. In this case the reduction in the inside diameter and hence the pressure in the input channel can be flexibly varied. The embodiment according to a) shows a valve, which may be an actively controlled or passive valve. In the case of a controlled valve it is also possible to flexibly vary the reduction in the inside diameter and hence the pressure in the input channel. The valve could also advantageously be synchronised with the voltage pulses in order to optimize the method according to the invention.

The transitions from the inner wall of the input channel to the region of the diminution are preferably designed so that they are rounded or flattened, as, e.g., in the embodiments according to FIG. 5 a) to d) to avoid sharp-edged transitions. This is particularly advantageous since otherwise the material to be treated could be damaged by excessive shearing forces.

Diminutions 55 can obviously be arranged at different points of the input channel. Moreover, it is also possible to arrange a plurality of diminutions in series in order to increase their effect.

Figure 6:
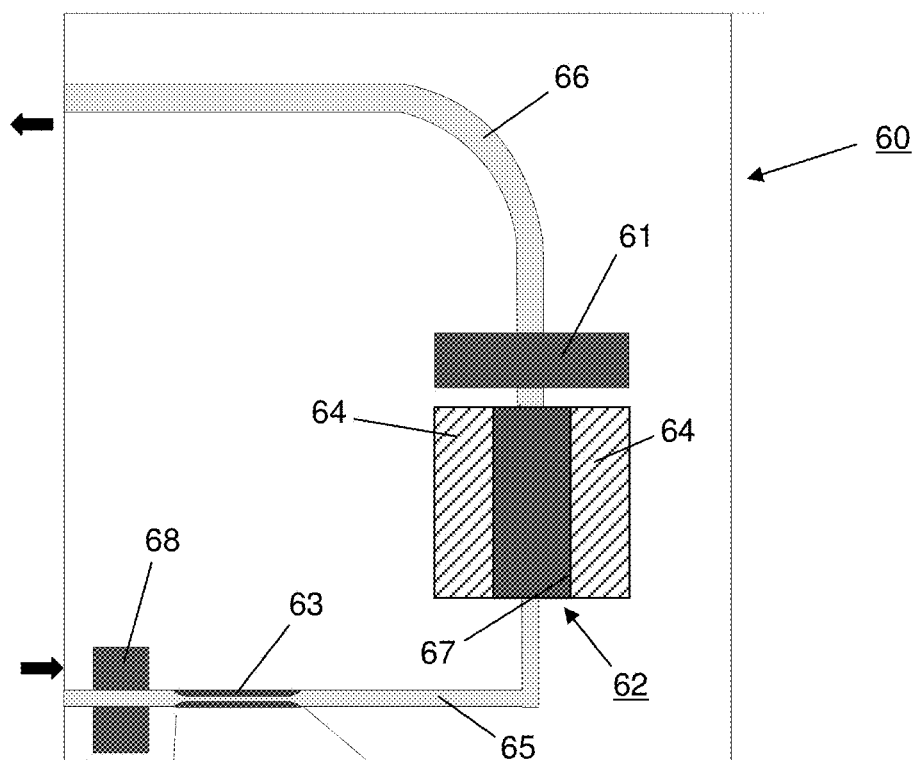
FIG. 6 shows a further embodiment of the device according to the invention with earthing electrodes.

FIG. 6 shows a further device 60 according to the invention which is in principle equivalent to device 1 according to FIG. 1, but additionally earthing electrodes 60, 61 are installed. In this advantageous embodiment it is clear that the earthing electrodes can be arranged at different points along the input and output channel. Thus, in this example earthing electrode 61 is arranged downstream directly at chamber 62, whilst earthing electrode 68 is arranged upstream in the vicinity of diminution 63. In addition, the gap between isolators 64 in this embodiment is wider than the inside diameter of input channel 65 and output cannel 66, so that the flow rate of the fluid in chamber 62 is reduced, resulting in an extension of the holding time of the fluid in interior 67 of chamber 62.

The invention claimed is:

1. Device with at least one electrode for generating an electrical field in a chamber comprising
    of at least one electrode in a chamber,
    at least one input channel for introducing a fluid into the chamber and
    at least one output channel for discharging the fluid from the chamber, wherein an average inside diameter of the at least one input channel is smaller than the average inside diameter of the at least one output channel, wherein the input channel has at least one diminution for reducing its inside diameter.

2. The device according to claim 1, wherein the inside diameter of the input channel is at least at one point smaller than the smallest inside diameter of the output channel.

3. The device according to claim 1, wherein the diminution comprises a reduction of an outside diameter of the input channel while at least approximately maintaining the wall thickness, and/or by elevations, bulges or the like arranged inside the input channel.

4. The device according claim 1, wherein an opening of the output channel is arranged above the chamber.

5. The device according to claim 1, wherein the output channel and/or the input channel is/are provided with at least one valve.

6. The device according to claim 5, wherein said at least one valve is a check valve.

7. The device according claim 1, wherein the input channel and/or the output channel is/are provided with at least one earthing electrode.

8. The device according to claim 1, wherein the at least one electrode provided, on its side facing away from the fluid, is provided with at least one cooling device.

9. The device according to claim 8, wherein a non-current conducting, heat conducting film is arranged between the electrode and the cooling device.

10. A method for electroporation or electrofusion of cells, cell particles and/or membrane vesicles comprising
    providing the device according to claim 1, and electroporating or electrofusing cells, cell particles and/or membrane vesicles in a flow-through process.

11. Device with at least one electrode for generating an electrical field in a chamber comprising
    of at least one electrode in a chamber,
    at least one input channel for introducing a fluid into the chamber and
    at least one output channel for discharging the fluid from the chamber, wherein an average inside diameter of the at least one input channel is smaller than the average inside diameter of the at least one output channel, wherein the output channel is designed in the shape of an arc or curve.

* * * * *